(12) United States Patent
Weber et al.

(10) Patent No.: US 8,603,830 B2
(45) Date of Patent: Dec. 10, 2013

(54) METHOD FOR THE DETERMINATION OF POLYSORBATE 80

(75) Inventors: Alfred Weber, Vienna (AT); Andrea Engelmaier, Vienna (AT); Heinz Anderle, Klosterneuburg (AT); Hans-Peter Schwarz, Vienna (AT)

(73) Assignees: Baxter International Inc., Deerfield, IL (US); Baxter Healthcare SA, Glattpark (Opfikon) (CH)

( * ) Notice: Subject to any disclaimer, the term of this patent is extended or adjusted under 35 U.S.C. 154(b) by 16 days.

(21) Appl. No.: 13/410,114

(22) Filed: Mar. 1, 2012

(65) Prior Publication Data

US 2012/0225487 A1   Sep. 6, 2012

Related U.S. Application Data

(60) Provisional application No. 61/449,535, filed on Mar. 4, 2011.

(51) Int. Cl.
*G01N 33/68* (2006.01)
*G01N 21/31* (2006.01)
*G01N 1/18* (2006.01)

(52) U.S. Cl.
USPC ............. 436/93; 436/84; 436/86; 436/106; 436/109; 436/110; 436/111; 436/164; 436/166; 436/174; 436/175; 436/177; 422/82.09

(58) Field of Classification Search
USPC ......... 436/84, 86, 91, 93, 106, 109, 110, 111, 436/127, 128, 131, 164, 166, 171, 174, 175, 436/177, 178; 422/68.1, 82.05, 82.09
See application file for complete search history.

(56) References Cited

U.S. PATENT DOCUMENTS

| | | | |
|---|---|---|---|
| 6,270,672 B1 * | 8/2001 | Turecek et al. | 210/645 |
| 7,531,358 B2 * | 5/2009 | Kakuta et al. | 436/86 |
| 2003/0133829 A1 * | 7/2003 | Anderle et al. | 422/28 |
| 2007/0082004 A1 * | 4/2007 | Morton et al. | 424/178.1 |

FOREIGN PATENT DOCUMENTS

| | | | |
|---|---|---|---|
| CN | 101639439 | * | 2/2010 |
| CN | 101839439 A | | 2/2010 |

OTHER PUBLICATIONS

International Search Report for International Patent Application No. PCT/EP2012/000898 mailed Jul. 20, 2012, 5 pages.
Kasuya, Y. et al., "Analytical method of determining polysorbates in foods by HPLC," *Tokyo-to KenboAnzen Kenkyu Senta Kenyu Nenpo*, 2009, vol. 59, pp. 137-142, Database Accession No. 2009:1005579, Abstract, 1 page.

* cited by examiner

*Primary Examiner* — Maureen Wallenhorst
(74) *Attorney, Agent, or Firm* — Morgan, Lewis & Bockius LLP

(57) ABSTRACT

The present invention relates to a method for the determination of polysorbate in a protein-containing sample. The method of the present invention involves the pretreatment of the sample by alkaline hydrolysis followed by colorimetric determination.

17 Claims, 6 Drawing Sheets

METHOD FOR THE DETERMINATION OF POLYSORBATE 80

CROSS REFERENCES TO APPLICATIONS

This application claims priority to U.S. Provisional Patent Application Ser. No. 61/449,535, filed Mar. 4, 2011, the disclosure of which is hereby expressly incorporated herein by reference in its entirety for all purposes.

FIELD OF THE INVENTION

The present invention relates to a method for the determination of polysorbate in a protein-containing sample. The method of the present invention involves the pretreatment of the sample by alkaline hydrolysis followed by colorimetric determination.

BACKGROUND OF THE INVENTION

Viral safety is a basic requirement for therapeutic proteins, especially for plasma-derived drugs. Over the recent years, substantial progress in virus safety had been made by almost eliminating the risk of virus transmission. Specific steps designed to remove or inactivate viruses were developed, validated and introduced in the manufacturing process of therapeutically used plasma proteins. The manufacturing processes of coagulation factors like factor VIII or factor IX, plasma proteinase inhibitors such as antithrombin, antitrypsin or C1-inhibitor, and of albumin and immunoglobulins must have at least one inactivation step effective against lipid-enveloped viruses to fulfill the safety requirement, and national and international regulatory bodies have set up a comprehensive framework of regulations to ensure maintenance and further improvement of virus safety. For example, the scientific Committee for Proprietary Medicinal Products (CPMP) as an organ of the European Medicines Agency (EMA) issued guidelines covering virus safety of biologicals. To minimize the risk of virus transmission by plasma-derived drugs, CPMP guidelines besides other preventive actions on the level of plasma as the starting material, strongly recommend the incorporation of two independently acting virus inactivation procedures in the manufacturing process.

The knowledge of the usefulness of detergents for viral inactivation together with the availability of chromatographic protein purification methods has shown the way to viral inactivation by detergents in plasma protein processing. The primary target viruses HIV, HBV, and HCV are all lipid-enveloped. Therefore, an effective virus inactivation strategy rationally takes advantage of viral susceptibility to detergent alone or to the well established solvent-detergent (S/D) procedure. The effect of all these procedures lies in the specific disruption of the viral lipid envelope, while having a relatively low impact on the integrity of therapeutic proteins with the exception of lipoproteins.

The non-ionic detergent polyoxyethylene sorbitan monooleate (polysorbate 80, Tween™ 80) is the most commonly used virucidal detergent of the polysorbates. Following the virus inactivation step, the manufacturing process has to comprise a purification step effective to remove the inactivation agents, such as chromatographic adsorption of the protein. In order to monitor the efficiency of the detergent removal procedure and also to check the compliance with the specified and validated limits of detergent concentration during the virus inactivation, however, the determination of the detergent has to be performed in the presence of varying and occasionally high concentrations of proteins, e.g. plasma proteins. The chemical composition and the structural diversity of polysorbates like polysorbate 80, the low reactivity of these compounds, the protein/buffer matrix as well as the possible presence of other physico-chemically related detergents such as e.g. alkylphenol ethers like Triton™ X-100 with varying numbers of ethylene oxide residues render the determination difficult. Concerns over risks associated with bovine spongiform encephalopathy (BSE) have led to the introduction of a vegetable-derived form of polysorbate 80 manufactured from plant fats instead of bovine tallow. Despite their equal virucidal effectivity these polysorbates with a presumably different fatty acid profile may diverge in analytical sensitivity.

An early colorimetric assay based on the formation of a complex between polysorbate 80 and starch and measurement of the excess free starch by its reaction with iodine has been adapted for tissue culture media and vaccines containing amino acids, sugars, and protein. Another colorimetric assay based on the complexation of polyoxyethylene chains with thiocyanatocobaltate(II) and extraction of the complex into chloroform has originally been developed to determine the concentration of polyethylene glycol fatty acid esters in aqueous solutions. Since then, its use has been extended to other polyethoxylated nonionic surfactants such as e.g. p-isooctylphenol polyoxyethylene ethers (available from various manufacturers under the trade names Triton™ X-100, Igepal™ CA-630, Nonidet™ P40, or Tergitol™ NP40), with diethyl ether, methylene chloride or chloroform as extractant.

The application of this method for biologicals is however limited by the presence of proteins, which strongly interfere and, therefore, have to be removed before performing the analysis. To overcome protein-related matrix effects, separation techniques were introduced such as a cold ethanol precipitation step for protein removal by centrifugation before thiocyanatocobaltate(II) colorimetry, size-exclusion chromatography with post-column colorimetric derivatization, size-exclusion chromatography with a base concentration of polysorbate 80 above the critical micellar concentration to prevent micellar aggregation and UV detection at 235 nm, protein-depletion chromatography of unbound polysorbate with capture of protein on an ion-exchange HPLC column, solid-phase extraction with delipidation, colorimetric derivatization and separation of the thiocyanatocobaltate(II) complex by gel permeation chromatography, acidic hydrolysis with HPLC or GC determination of the fatty acid, or mild saponification with HPLC determination of the released fatty acid, thin-layer chromatography, or liquid extraction with HPLC separation and mass spectrometric detection. The latter approaches, which rely on the fatty acid moiety of polysorbate, are impeded by varying fatty acid compositions of the analyte. Another recent approach measures fluorescence polarization of 5-dodecanoylaminofluorescein incorporated into polysorbate micelles. However, these methods are either very time-consuming, suffer from limited sample throughput, or require complex instrumentation and separate validation of each step.

Therefore, a strong need exists to provide a method for the determination of polysorbate in protein-containing samples by a colorimetric assay, wherein the interference of protein can be eliminated in a fast and simple manner. Such a method should allow for the determination of the actual detergent concentration during e.g. virus inactivation, as well as in the final concentrates of purified proteins.

This need is satisfied by providing the embodiments characterized in the claims.

SUMMARY OF THE INVENTION

The present invention relates to a method for the determination of polysorbate in a protein-containing sample which is based on a pretreatment of the sample by alkaline hydrolysis followed by the colorimetric determination.

DETAILED DESCRIPTION OF THE INVENTION

The present invention relates to a method for the determination of polysorbate in a protein-containing sample, comprising the steps:
(a) subjecting the sample to alkaline hydrolysis;
(b) neutralizing the sample after alkaline hydrolysis;
(c) optionally removing denatured precipitate from the neutralized sample;
(d) adding an aqueous mixture of a thiocyanatometal complex to the optionally filtered sample to form a sorbitan polyoxyethylenethiocyanatometal complex;
(e) extracting said sorbitan polyoxyethylenethiocyanatometal complex formed in step (d) into a non-water miscible organic solvent;
(f) measuring the absorbance of the extract obtained in step (e) to quantify the amount of said sorbitan polyoxyethylenethiocyanatometal complex formed in step (d); and
(g) calculating the amount of the polysorbate contained in the sample from the amount of said sorbitan polyoxyethylenethiocyanatometal complex determined in step (f).

The term "polysorbate" as used herein relates to any polyoxyethylene sorbitan fatty acid esters (polysorbates). Preferred polysorbates include polysorbate 20, 40, 60, and 80. Polysorbate 80 is particularly preferred. Said polysorbate 80 may originate from animals or from plants.

The term "protein-containing sample" as used herein relates to any sample that contains at least one protein. The sample may for example be derived from a process for the production of recombinant proteins, wherein the sample may be taken at any stage of said process, or may be the final product of said process. Further, the sample may for example be derived from a process for the production of blood plasma-derived proteins, wherein the sample may be taken at any stage of the process, or may be the final product of said process. Preferably, the sample is taken after a step of virus inactivation in a process for the production of blood plasma derived proteins. Accordingly, the protein(s) contained in the sample may be one or more blood plasma protein(s). Further, the protein-containing sample may be blood plasma. Furthermore, the protein-containing sample may be a sample containing vaccines and/or peptides.

The protein-containing sample may further contain isooctylphenol polyoxyethylene ether (Triton™ X-100) and/or tri-n-butyl phosphate (TNBP), which may have been added for example in a step of virus inactivation in a process for the production of blood plasma derived proteins.

As large molecules like proteins may contain structural entities, built up by a set of hydrophobic and hydrophilic amino acids, which might mimic detergent characteristics, they might also interfere in such determination assays. The binding of detergent to protein structures may also influence the determination by preventing complex formation resulting in lower recoveries of the analyte. Therefore, prior to the colorimetric determination, the concomitant proteins have to be destroyed in order to provide unbiased results to prevent this interference. Protein precipitation using a solvent like ethanol is one possibility to remove the protein prior to perform the assay. However, given the fact that complex protein mixtures may also contain low molecular weight proteins such as apolipoprotein A1 or proteins like α1-acid glycoprotein which hardly precipitate at useful concentrations of ethanol, the application of this sample preparation step is fairly limited. Instead, the present invention adopts a sample pretreatment relying upon alkaline hydrolysis, particularly at elevated temperatures. Under those conditions as later further exemplified, proteins will be destroyed to an extent that they no longer can exert their interfering influence on the assay. Although the hydrolysis applied will not result in total breakdown of the protein into amino acids, it was surprisingly harsh enough to eliminate false positive reactions as well as binding of the detergent.

Preferably, step (a) of the method of the present invention, i.e. subjecting the sample to alkaline hydrolysis, comprises treating the sample with an alkaline agent at elevated temperatures for a specific duration of time. Preferably, the alkaline agent is selected from the group consisting of NaOH, KOH, LiOH, $Ba(OH)_2$, $Sr(OH)_2$, $Ca(OH)_2$, tetramethylammonium hydroxide, tetraethylammonium hydroxide, tetrapropylammonium hydroxide, tetrabutylammonium hydroxide, and homologous and heterologous substituted quaternary alkyl- and cycloalkylammonium hydroxides. More preferably, the alkaline agent is NaOH, preferably at least 3 N NaOH, more preferably about 10 N NaOH. The elevated temperature is preferably at most 100° C. and at least about 80° C., more preferably at least about 90° C., most preferably at least about 95° C. In a particularly preferred embodiment, alkaline hydrolysis is performed at about 95° C. to about 100° C. The duration of alkaline hydrolysis is preferably at least about 15 minutes, more preferably at least about 30 minutes, most preferably at least about 45 minutes. Further, the duration of alkaline treatment is preferably at most 120 minutes, more preferably at most 90 minutes. In a particularly preferred embodiment, the duration of alkaline treatment is between about 45 to about 90 minutes, more preferably between about 45 minutes and 75 minutes, more preferably between about 50 minutes and 70 minutes, and most preferably 60 minutes.

Step (b) of the method of the present invention, i.e. neutralizing the sample after alkaline hydrolysis, preferably comprises neutralizing the sample with an acid, e.g. acetic acid, to a pH between about 7 and about 8. Further acids that can be used in this context include formic acid, propionic acid, butyric acid, lactic acid, hydroxybutyric acid, alkane- and cycloalkane monocarboxylic acid, dicarboxylic acids and tricarboxylic acids.

Preferably, step (c) of the method of the present invention, i.e. removing denatured precipitate from the neutralized sample, can be done by filtration or centrifugation, if actually performed since it depends on the protein solution, comprises centrifugation of the sample or filtering the sample with a filter that does not bind polyoxyethylene sorbitan. In a preferred embodiment, the filter is a hydrophilic filter, e.g. a filter made of cellulose acetate. The pore size of the filter is not particularly limited, as long as precipitate is sufficiently withheld, and may be e.g. 0.22 μm.

The thiocyanatometal complex added in step (d) is preferably an aqueous mixture of $Co(NO_3)_2.6H_2O$ and $NH_4SCN$ and the sorbitan polyoxyethylenethiocyanatometal complex formed is a sorbitan polyoxyethylenethiocyanatocobaltate (II) complex.

The aqueous mixture of $Co(NO_3)_2.6H_2O$ and $NH_4SCN$ preferably added to the filtered sample in step (d) of the method of the present invention preferably contains about 1% (w/v) to about 4% (w/v), preferably about 1.5% (w/v) to about 4% (w/v), more preferably about 2% (w/v) to about 4% (w/v), and most preferably 3% (w/v) $Co(NO_3)_2.6H_2O$ and about 10% (w/v) to about 30% (w/v), preferably 15% (w/v) to about 25% (w/v), more preferably about 20% (w/v) $NH_4SCN$ in distilled water.

Preferably, the non-water miscible organic solvent used in step (e) of the method of the present invention for the extraction of the sorbitan polyoxyethylenethiocyanatometal complex formed in step (d) is selected from the group consisting of chloroform, methylene chloride, o-dichlorobenzene, bromoform, and trichloroethylene, wherein methylene chloride is particularly preferred.

Further, the absorbance of the extract obtained in step (e) of the method of the present invention is preferably measured in step (f) in a range of between about 300 nm and about 340 nm, more preferably between about 310 nm and about 330 nm, most preferably at about 324 nm. Methods for measuring the absorbance of a sample at one or more particular wavelength(s) are known to a person skilled in the art and include for example the use of a standard UV/VIS-spectrophotometer.

Further, methods for performing step (g) of the method of the present invention, i.e. calculating the amount of the polysorbate contained in the sample from the amount of said sorbitan polyoxyethylenethiocyanatometal complex determined in step (f), are known to a person skilled in the art.

In a preferred embodiment, the method of the present invention further comprises after step (a) and before step (b) a step of cooling the sample after alkaline hydrolysis, preferably to room temperature. Further, the method of the present invention may comprise after step (b) and before step (c) a step of keeping the sample at room temperature for at least 15 minutes, preferably at least 30 minutes, in order to allow the complete formation of possible denatured precipitate.

In order to avoid losses of analyte due to unspecific adsorption of any polysorbate to the surface of the sample container, e.g. to a plastic surface, the method of the present invention may comprise a step of mixing the sample with a protein solution, e.g. an albumin solution, before alkaline hydrolysis. Such adsorption may particularly occur with samples having a low protein content, e.g. a protein content below 1 mg/ml.

Further, the method of the present invention may comprise a step of establishing a standard curve using samples having known concentrations of polysorbate and one or more proteins for calibration of the absorbance measurements. Methods for establishing a respective standard curve are known to a person skilled in the art.

The figures show:

FIG. 1 shows the results of colorimetric polysorbate measurement after hydrolysis times between 15 and 120 min at 100° C. Data points are the mean of two independent hydrolysis mixes which differed less than 4% when alkaline hydrolysis was done for at least 60 minutes.

Figure 1:
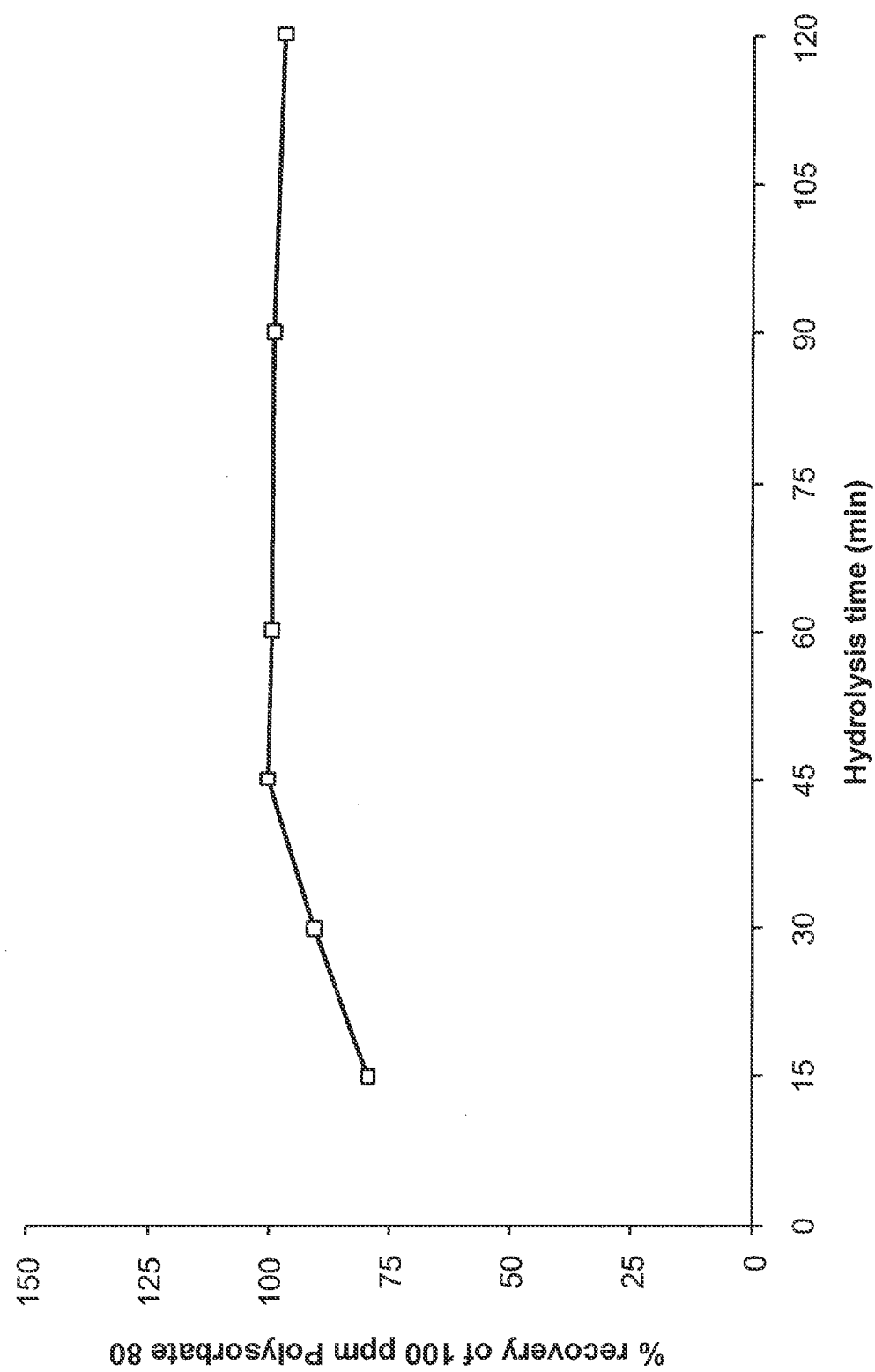

FIG. 4 shows the calibration curves of polysorbate 80 and Triton™ X-100 without sample pretreatment (A), as well as of polysorbate 80 and a mixture of polysorbate 80, tri-n-butyl phosphate (TNBP) and Triton™ X-100 after alkaline hydrolysis (B).

The present invention will be further illustrated in the following examples without any limitation thereto.

EXAMPLES

Materials:

All chemicals used were of analytical grade unless stated otherwise. NaOH, 96% acetic acid, cobalt nitrate hexahydrate ($Co(NO_3)_2 \cdot 6H_2O$), methylene chloride (Lichrosolv™), Triton™ X-100, tri-n-butyl phosphate (TNBP) and ammonium thiocyanate ($NH_4SCN$) were purchased from Merck (Germany). Two lots of polysorbate 80 (Tween™ 80) from bovine as well as from vegetable source were purchased from ICI (USA). Aqueous solutions of the detergent with a content of 1% (w/v) were prepared and subsequently used for analysis.

The influence of several plasma proteins on the accuracy of the assay was investigated using plasma protein fractionation intermediates and concentrates from Baxter BioScience (Vienna, Austria). Briefly, the following human plasma protein concentrates were used to investigate the suitability of the sample pretreatment by alkaline hydrolysis: albumin, immunoglobulin, antithrombin, protein C, developmental activated and non-activated prothrombin complex concentrate (aPCC and PCC), high-purity factor IX concentrate, and orosomucoid ($\alpha_1$-acid glycoprotein). Finally, the method was also performed in whole plasma, using lyophilized human reference plasma supplied by Baxter (Baxter BioScience Diagnostics Division, Vienna, Austria).

The alkaline hydrolysis itself was carried out in 100×15 mm polypropylene tubes with screw caps (Greiner, Austria), and the subsequent colorimetric determination in glass tubes with screw caps. Filters used were 0.22 µm MINISART (Sartorius, Germany). The colorimetric measurement was done on a LKB Ultrospec K4053 spectrophotometer using 1 cm Suprasil quartz cells with screw-caps (Hellma, Germany). Room temperature (20-25° C.) was kept during all steps of the procedure except the hydrolysis.

Example 1

Alkaline Hydrolysis

Into a polypropylene tube containing 1 ml sample, standard or control with a polysorbate content of less than 400 mg/L=400 ppm, 0.5 ml 10 M NaOH was added. The solution was kept in a boiling water bath for 60±10 min. After chilling to room temperature, the alkaline hydrolysates were neutralized to pH~7 to 8 with 0.5 ml 10 M acetic acid by checking the pH with indicator strips (Merck, Germany). Following the neutralization, the samples were kept at room temperature for at least 30 min. Depending on the protein solution, a precipitate occurred, which was removed by filtration using a Minisart 0.22 µm filter prior to the procedure of the colorimetric determination. Samples with a protein content of less than 1 mg/mL were mixed with an albumin solution before hydrolysis in order to avoid losses of analyte due to unspecific adsorption to plastic surfaces, which might occur during the procedure. Addition of 0.1 ml of a human albumin solution with a concentration of 200 mg/ml to 1 ml of the respective sample proved to be effective for the prevention of unspecific losses of polysorbate 80. This dilution of the sample has to be taken into account upon calculation of the polysorbate concentration of the sample.

Example 2

Colorimetric Measurement

The colorimetric determination was performed as follows. Briefly, 1 ml of a neutralized protein hydrolysate or an aqueous polysorbate solution, which contained essentially no protein, was mixed with 3 ml thiocyanatocobaltate reagent. This reagent contained 3% (w/v) Co(NO$_3$)$_2$.6H$_2$O and 20% (w/v) NH$_4$SCN dissolved in distilled water, and was prepared freshly every day. Then, 2 ml methylene chloride were added. After vigorous shaking, the phases were allowed to separate for at least 30 min at 20-25° C. Finally, the methylene chloride phase was measured spectrophotometrically in screw-capped cuvettes against a methylene chloride blank at 320 nm.

Example 3

Calibration of the Assay

The assay was calibrated by analyzing standard dilutions covering a range from 10 to 400 ppm polysorbate 80. These standard solutions were prepared by spiking a protein solution with aqueous polysorbate solutions. As the hydrolysis conditions described here virtually destroy the influence of any protein solution tested so far, any protein solution, including whole plasma, should be suitable. However, following the principle to compare like versus like, a plasma protein solution was selected, which was as similar as possible to the solution of interest. Thus, a standard curve covering a range of 10 to 400 ppm polysorbate 80 containing the concentrations 5, 10, 20, 50, 100, 200 and 400 ppm was constructed using developmental PCC and analyzed in duplicate each time the assay was performed.

Example 4

Optimization of Hydrolysis Time

In order to establish an appropriate hydrolysis time, developmental aPCC (activated Prothrombin Complex Concentrate) was selected as a protein matrix already known to interfere substantially with the colorimetric determination of polysorbate 80. Although this matrix essentially contained no detergent, a false positive reaction was observed upon analysis of this solution after attempted protein removal by precipitation with ethanol. With a protein concentration of about 25 mg/ml, this matrix, which contains a broad spectrum of different plasma proteins, such as prothrombin, inter-α-trypsin inhibitor, complement, and vitronectin, was spiked with 100 ppm polysorbate 80. Alkaline hydrolysis was performed as described, keeping samples between 15 and 120 min in the boiling water bath. The further processing was done as described above.

The results of colorimetric polysorbate measurement after hydrolysis times between 15 and 120 min at 100° C. are shown in FIG. 1. The selected protein matrix, which was already known to contain components yielding a false positive reaction upon determination after protein precipitation with ethanol, showed no false positive reaction even after very short hydrolysis times. After a hydrolysis of 15 minutes at 100° C., the added 100 ppm polysorbate 80 could not be recovered entirely, and only 79% of the spiked amount was found. This level of recovery was the lowest found in the study, and additionally showed a higher standard deviation compared to all other recoveries obtained after prolonged hydrolysis. Thus, the short alkaline hydrolysis was not sufficient to completely eliminate protein interference on the assay, and a lower recovery was observed, indicating that probably a relatively tight association between protein and detergent might prevent the participation of the detergent in the colorimetric determination. However, alkaline hydrolysis performed over 30 min yielded a recovery of 90%, and the following samples analyzed after 45, 60, 90 and 120 min, respectively, showed recoveries of 100%, 99%, 99% and 97%, respectively, each value characterized by a coefficient of variation below 2.5%. According to these findings a hydrolysis time of 60±10 min was chosen for all further experiments.

Example 5

Assay Accuracy in Different Plasma Protein Matrices

Official guidelines for method validation define that the accuracy of an analytical procedure expresses the closeness of agreement between a true value and the value found. There are several approaches to assess the accuracy of an analytical method. As there is no certified reference material for polysorbate 80 in the presence of plasma proteins, the approach of spiking a blank reference sample with a known concentration of analyte was followed. This approach of spiking relevant protein solutions was chosen because of the already known influence of proteins on the assay. Due to the differences in primary, secondary, and tertiary structure, the resistance of proteins against treatment with alkali might differ considerably, with the procedure applied for polysorbate 80 determination being less vigorous than the total alkaline hydrolysis comprising heating for 15 hours at 120° C.

In order to investigate whether the conditions of alkaline hydrolysis used here were sufficient to allow the accurate analysis of polysorbate 80 in very different protein matrices, plasma protein solutions including albumin, immunoglobulin, orosomucoid, antithrombin, protein C and clotting factors as well as whole plasma were employed to check the recovery of polysorbate 80. The protein concentration of the investigated samples ranged from 1 to 50 mg/mL. Table 1 contains the results of the spiking experiments, in which 10 ppm, 50 ppm, 100 ppm or 200 ppm polysorbate 80 were added to the blank matrices.

TABLE 1

Recovery of polysorbate 80 (p80) in different plasma protein solutions

| Plasma protein | concentration [mg/ml] | Recovery of polysorbate 80 [% of added amount] | | | |
|---|---|---|---|---|---|
| | | 10 ppm p80 | 50 ppm p80 | 100 ppm p80 | 200 ppm p80 |
| plasma | 30 | —*) | — | 106 | 104 |
| activated PCC | 30 | 94 | — | 104 | — |
| activated PCC | 10 | 100 | — | 106 | — |
| albumin | 20 | — | — | 102 | 100 |
| IgG | 20 | — | — | 90 | 93 |
| PCC | 30 | — | — | 98 | 96 |
| antithrombin | 20 | — | 99 | 98 | — |
| protein C | 6 | — | 99 | — | — |
| orosomucoid | 50 | — | 99 | — | — |
| conc. factor IX | 1 | — | 102 | — | — |

*)—: not determined

In all protein solutions investigated, recoveries between 90% and 106% of the added amount of polysorbate 80 were found. With these results, all the samples tested fulfilled criteria for the recovery data as a function of analyte concentration published by the AOAC (American Association of Official Analytical Chemists). According to these specifications, 100 ppm of analyte should be recovered with 90% to 107%, whereas the limits for the recovery of 10 ppm are 80% to 110% in order to guarantee a reliable result. Our results demonstrate that the hydrolysis conditions applied are suitable to eliminate the disturbing influence of protein, irrespective of the kind of the protein, at least in the protein concentrations investigated. This was shown even in the plasma matrix, known to be very complex and containing several hundred different proteins, but also low molecular weight components. The added amounts of 100 ppm as well as 200 ppm polysorbate 80 could be recovered with deviations less than 6%. Moreover, none of the purified proteins spiked with polysorbate did hinder a successful recovery, although structurally unrelated proteins were tested at different concentrations. Thus, for example the highly glycosylated protein orosomucoid, a very acidic protein with an isoelectric point beyond 3 known to bind diverse drugs, as well as albumin, which can bind fatty acids, did not inhibit the determination, even at the high concentrations employed. Even at a spiking concentration of 10 ppm polysorbate 80, which is the limit of quantitation, the assay gave accurate results independent of the protein concentration present. Developmental aPCC in concentrations of 10 and 30 mg protein/mL was spiked with 10 ppm polysorbate, and irrespective of the protein concentration in the assay, recoveries of 94% and 100% were obtained, thus again fulfilling the recommendations of the AOAC given above.

Example 6

Assay Precision and Linearity

Figure 2:
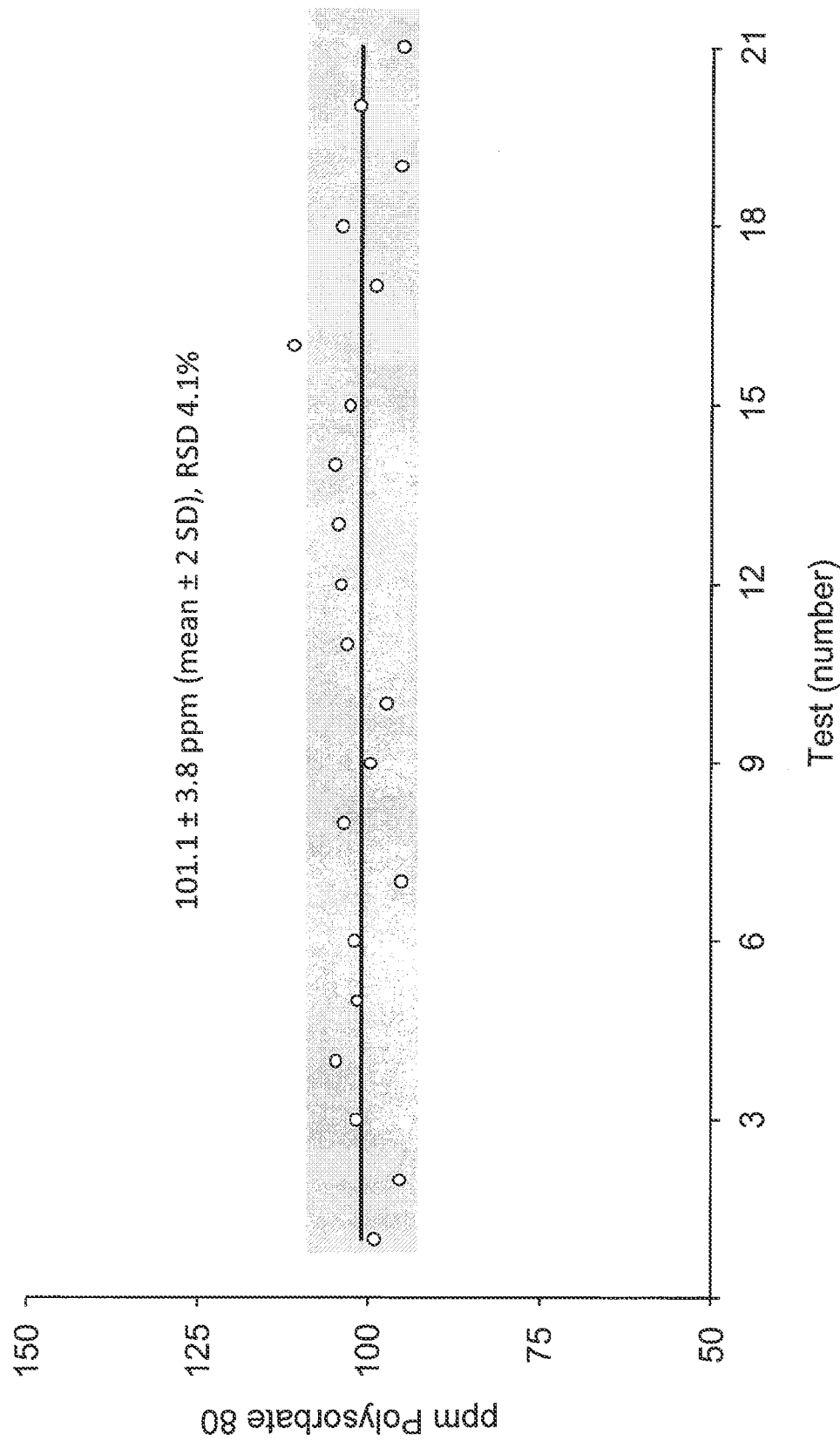
FIG. 2 shows the results of 21 determinations of a control sample containing 100 ppm polysorbate 80 to determine the precision and linearity of the assay. The range of two standard deviations of the mean is indicated.

According to official guidelines for validation of analytical methods, the precision of a method is the extent to which the individual test results of multiple determinations of series of samples agree, whereas the linearity of an analytical procedure describes its ability to obtain test results which are directly proportional to the concentration of the analyte in the sample. In order to describe these essential performance parameters of the assay, a control sample with 100 ppm polysorbate 80 in developmental PCC was used. The results of the analysis are shown in FIG. 2. Using 21 determinations of the control sample, the average of the sample had a relative standard deviation (sd) of 4.0% and 3.7% for inter- and intra-assay precision, respectively. Both deviations comply with the recommendation given by the AOAC, which is 5.3% for the precision within or between days measuring 100 ppm analyte. Only one of 21 determinations yielded a value outside the range defined by the double standard deviation, but was included in the mean±3 sd range. The diagram shows also the intra-assay variations marked by the error bars. The precision of the assay was further investigated at a concentration of 20 ppm, wherein a value of 3.0% was found. The analysis of a sample drawn during the inactivation process with the high concentration of 150 g polysorbate 80/L was analyzed with an average standard deviation of 2.9% (n=6), thus confirming that the method is also suitable to measure high concentrations occurring during virus inactivation process.

The calibration plots of the assay covering a range of 5 to 400 ppm polysorbate 80 show a good linearity, yielding a mean correlation coefficient r=0.999 (n=21) between concentration and measured extinction at 320 nm. The slope of the line was characterized by an inter-assay variation of 7.7% (n=21) and the limit of quantitation (LOQ) was found to be 10 ppm±0.4 ppm as calculated according to ICH recommendations.

Example 7

Comparison of Polysorbate of Different Origin

To evaluate if the origin of polysorbate 80 impacts the performance of the analysis, batches from vegetable and bovine source were compared. Both forms were analyzed in the presence of the above described protein solution following the same alkaline hydrolysis procedure. Additionally, the colorimetric determination with the thiocyanatocobaltate reagent was performed without sample pretreatment in the absence of proteins, thus mimicking conditions present after the temptative ethanol precipitation to remove protein.

Polysorbate 80 preparations initially used for virus inactivation had been produced from bovine tallow. With the appearance of bovine spongiform encephalitis (BSE), it became essential to avoid bovine material in the manufacturing of therapeutic proteins and to change to vegetable-derived detergent. Polysorbate 80 has since then been available in both forms, and plant-derived Tween 80 is already used in the virus inactivation processes in biopharmaceutical manufacturing.

Figure 3A:
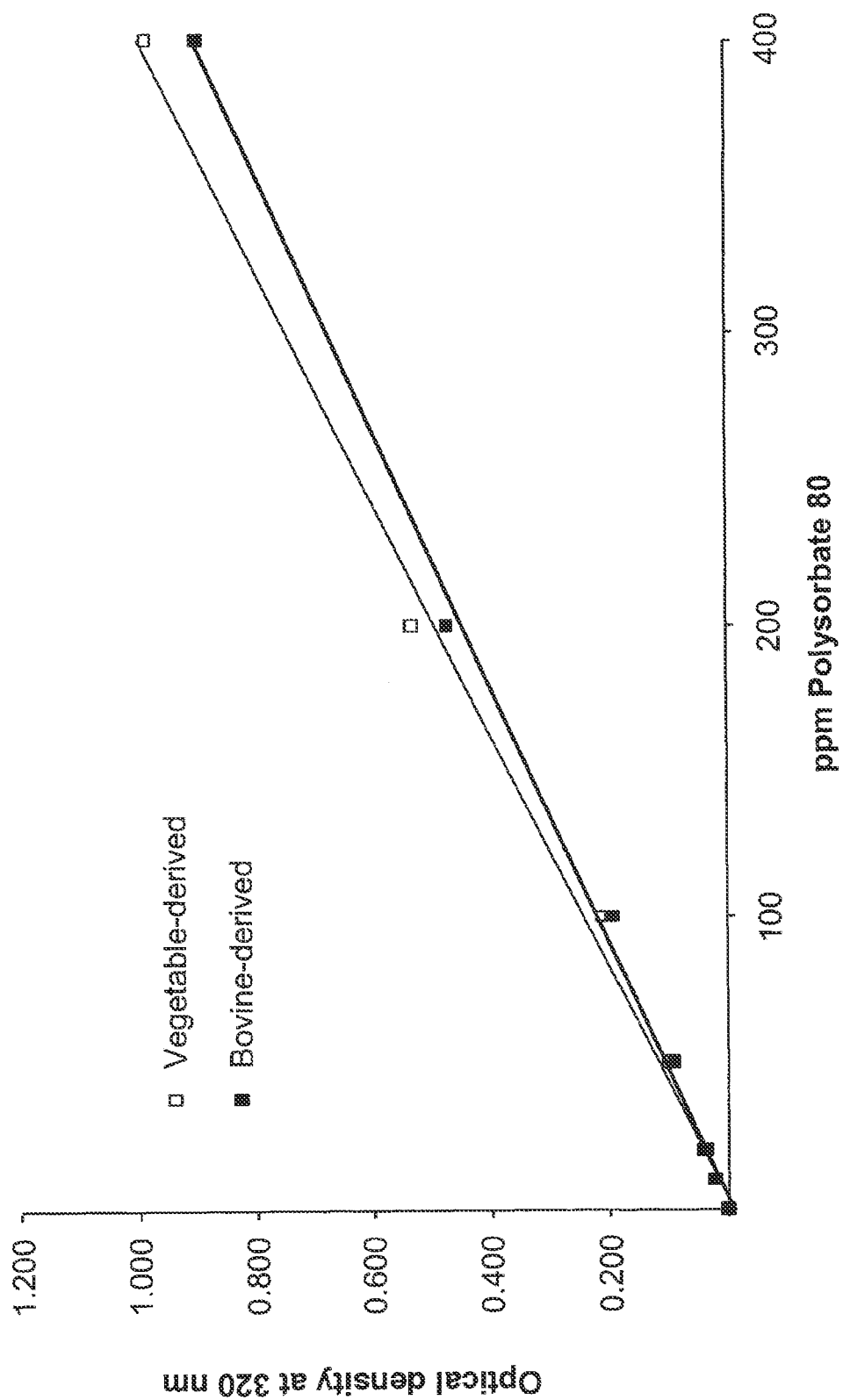
FIG. 3 shows calibration plots of samples spiked with polysorbate 80 derived from bovine and vegetable sources, respectively, with (B) or without any sample pretreatment (A).
Figure 3B:
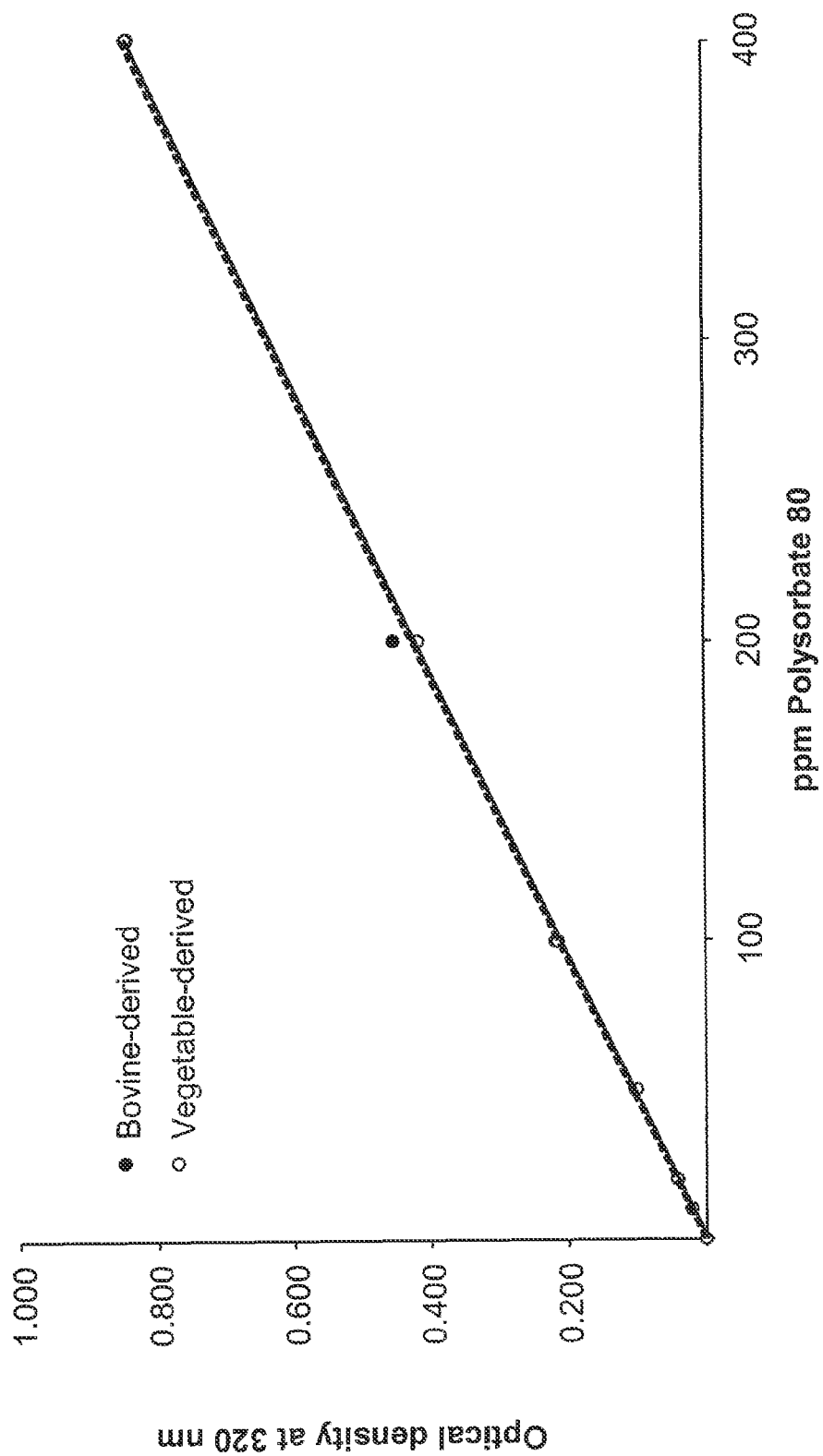

In order to assess the impact of this change to plant fats as the source material, which differ from tallow in the composition of constituting fatty acids and might display a presumably different fatty acid profile of the oleic acid-rich fraction, the reactivity of both polysorbate preparations was compared using an assay without any further sample pretreatment. The results are shown in FIG. 3A, in which both calibration plots are shown. The obtained plots differ in their slopes: the plant-derived polysorbate shows an obviously higher response comparing equal amounts of material, yielding a slope of 0.0025 compared to 0.0023 of animal-derived detergent. Moreover, upon analysis of several lots of both polysorbates, it could be confirmed that this observation was not batch-related. These findings were further supported by the results shown in FIG. 3B, in which both calibration plots obtained after alkaline hydrolysis are shown to be indistinguishable.

The sensitivity of the assay expressed in terms of the slope of the calibration plot is somewhat lower than without alkaline hydrolysis. Thus, an average slope of 0.0021 was found after alkaline hydrolysis, which is lower than the value obtained without hydrolysis. This suggests that the unhydrolyzed fatty acid part of the detergent might also be involved in the formation or influence the extractability of the complex.

Example 8

Evaluation of Assay Selectivity with Respect to Triton™ X-100

The selectivity of the assay in regard to the closely related detergent isooctylphenol polyoxyethylene ether (Triton™ X-100) as well as to the solvent tri-n-butyl phosphate (TNBP), both being included in the established solvent-detergent process for virus inactivation, was investigated. Thus, aqueous solutions containing Triton™ X-100 and polysorbate 80 were analyzed without alkaline hydrolysis in order to evaluate the selectivity of the colorimetric determination. Furthermore, the response of a ternary solvent-detergent inactivation mixture containing Triton™ X-100, polysorbate 80 and TNBP in the ratio 1:0.3:0.3% (w/v) was compared with a polysorbate 80 solution after alkaline hydrolysis. Again, developmental aPCC in a protein concentration of approximately 25 mg/ml served as protein matrix. Finally, the influence of very high concentrations of Triton™ X-100 on the assay after sample pretreatment with alkaline hydrolysis was evaluated both in the presence and absence of protein. For this experiments, Triton™ X-100 concentrations of 100, 300, 1000, 2000, 5000 and 10000 ppm were applied.

Figure 4A:
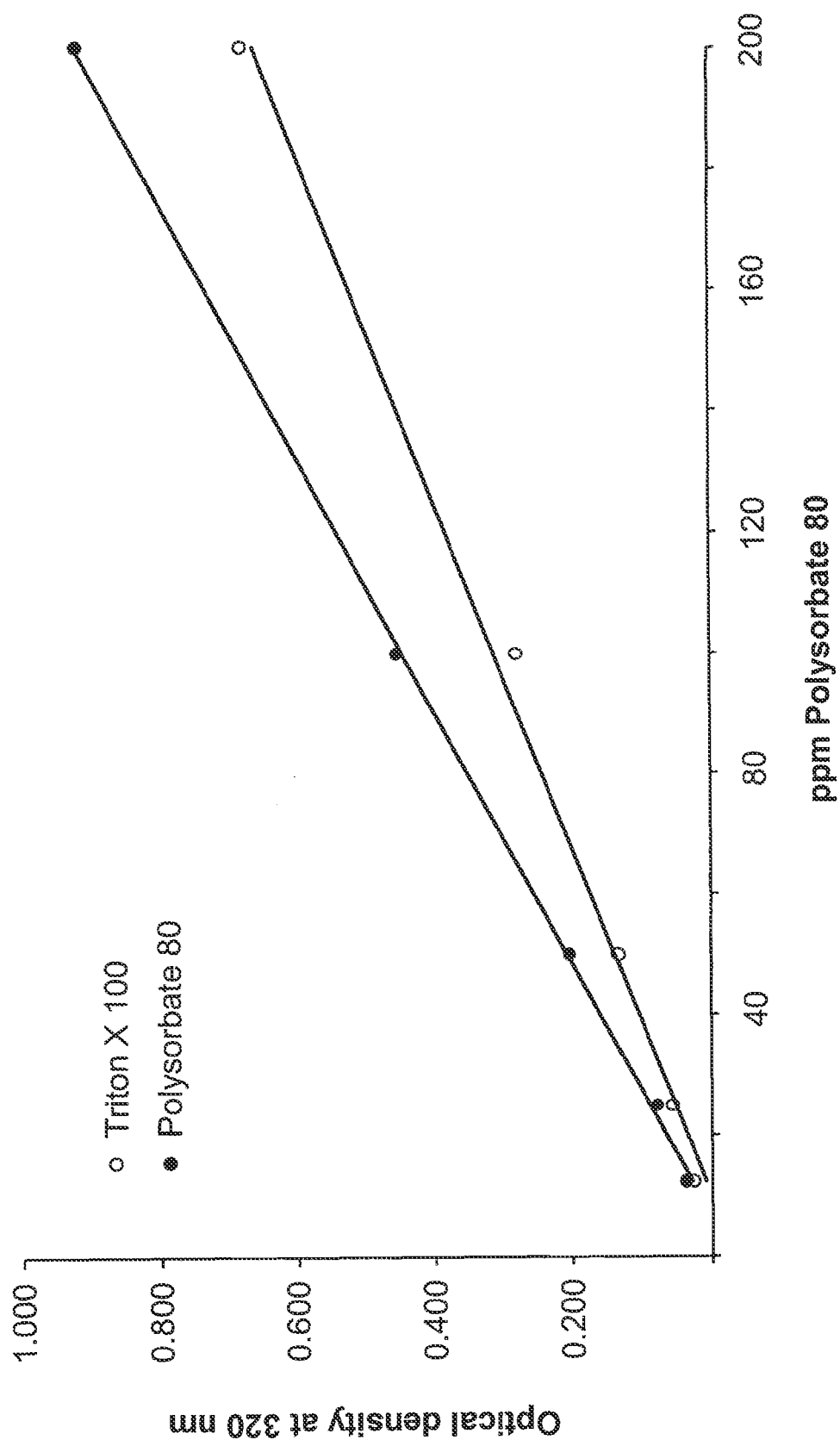

A very commonly used solvent-detergent (SD) virus inactivation mixture consists of a ternary formula of TNBP and the two closely related detergents Triton™ X-100 and polysorbate 80. Therefore, it became of interest whether the assay is capable of discriminating between these structurally related detergents. Both contain polyethoxy groups, which are involved in the colorimetric determination, so that Triton™ X-100 can, not surprisingly, be detected by the original assay as well. FIG. 4A compares the response of both detergents in the assay without any sample pretreatment. The reactivity of both detergents measured in the range of 12 to 200 ppm differed markedly. Triton™ X-100 gave only about 70% of the response of polysorbate 80 over the whole range of concentrations.

Figure 4B:
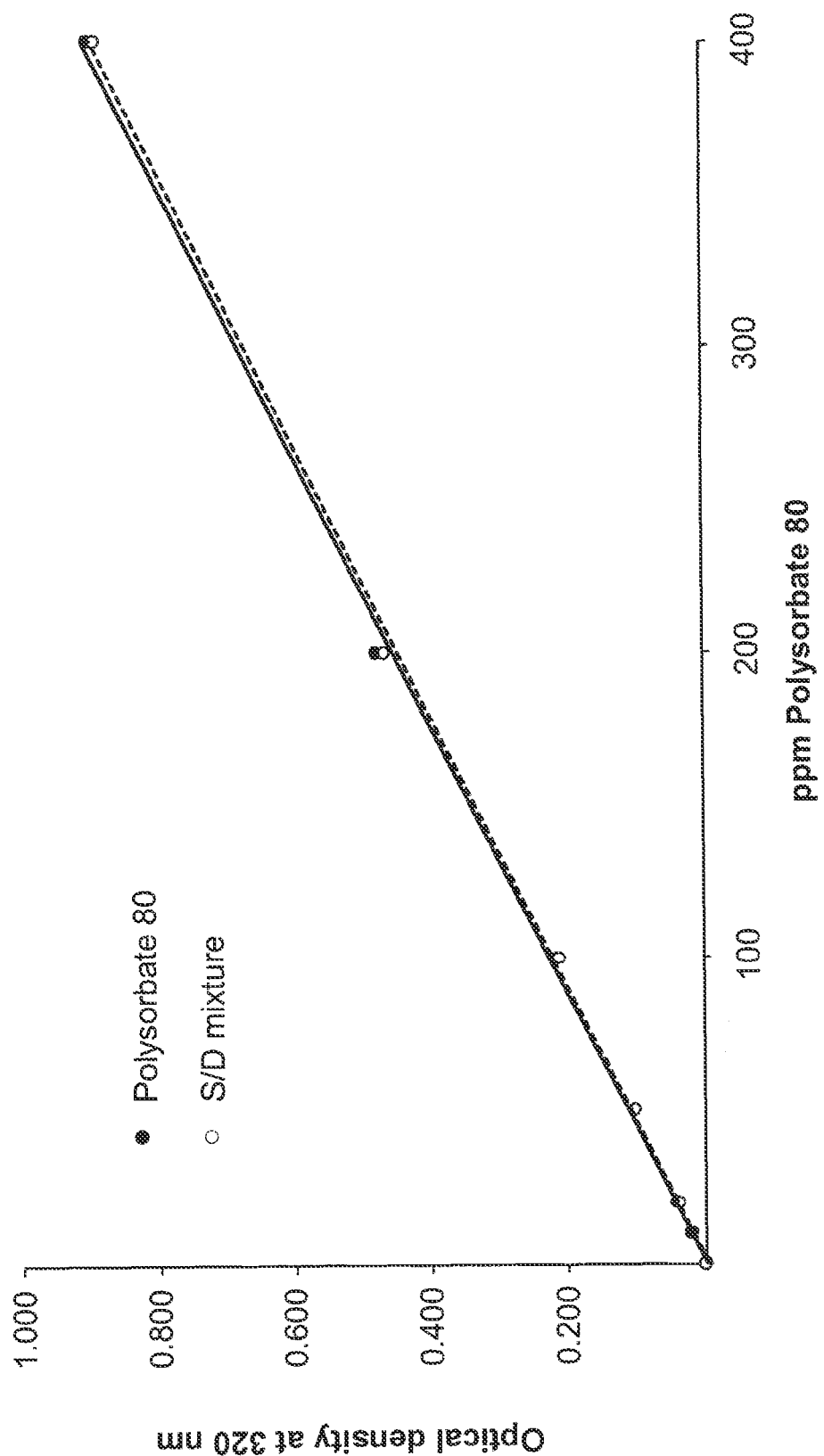

Due to these findings, and particularly to the fact that both detergents have different response factors, the original assay cannot be used if both detergents are present. A totally different effect is observed if the sample pretreatment by alkaline hydrolysis is included in the assay. FIG. 4B gives the calibration plot of the already above described SD mixture consisting of Triton™ X 100, polysorbate 80 and TNBP in the ratio 1.0:0.3:0.3% (w/v) in comparison with polysorbate 80 alone. Essentially no difference can be noticed comparing the relevant parameters slope and intercept of the calibration plots. As shown in Table 2, neither the slope, being in both cases 0.0023, nor the intercept, being −0.005 for polysorbate and −0.007 for the SD-mixture, differ.

TABLE 2

Reactivity of Triton ™ X-100 with and without alkaline hydrolysis

| | without hydrolysis | | with hydrolysis | |
|---|---|---|---|---|
| | polysorbate 80 | Triton ™ X-100 | polysorbate 80 | SD solution |
| slope | 0.0048 | 0.0035 | 0.0023 | 0.0023 |
| intercept | −0.0309 | −0.0358 | −0.005 | −0.007 |

These results show that in spite of the three times higher concentration of Triton™ X-100, the assay can be applied to analyze the polysorbate 80 concentration in the SD-mixture without any detectable interference by the closely related detergent Triton™ X-100. Surprisingly, the alkaline hydrolysis is capable to enhance the selectivity of the colorimetric determination. Additional experiments were performed to clarify whether the reactivity of Triton™ X-100 is destroyed completely or to a certain extent only. As summarized in Table 4, solutions containing less than 300 µg/ml Triton™ X-100 did not show any measurable response and, accordingly, had no impact on the values measured. Thus the alkaline hydrolysis led to an substantial increase in selectivity of the assay as shown by the experiment, where a 30-fold excess of Triton™ X-100 did not show any measurable impact even on the signal of only 10 ppm polysorbate 80. Even concentrations of Triton™ X-100 between 1000 and 10000 ppm, which were by far exceeding the calibrated concentration range of polysorbate 80, were found to react only moderately, proving that almost 99% of the reactivity of Triton™ X-100 were removed by the alkaline hydrolysis performed prior to the colorimetric determination.

TABLE 3

Reactivity of Triton ™ X-100 after alkaline hydrolysis

| ppm Triton ™ X-100 | 100 | 300 | 1000 | 2000 | 5000 | 10000 |
|---|---|---|---|---|---|---|
| % recovery | <5 | <1.7 | 1.5 | 1.3 | 1.5 | 1.4 |

Conclusions

The results of the above experiments with different hydrolysis times (cf. Example 4) showed that an alkali treatment as short as 15 min already was sufficient to reduce the influence of a given protein solution, which was previously shown to cause a clear overestimation of the polysorbate concentration by applying protein precipitation with ethanol. It could be demonstrated that with numerous proteins different in charge and size, polysorbate 80 could be analyzed without substantial interference of the protein matrix (cf. Example 5). In particular, 50 µg polysorbate 80/mL could be determined with a recovery of 99% in orosomucoid ($\alpha_1$-acid glycoprotein) at a protein concentration of about 50 mg/ml. The fact that this very acidic protein could be analyzed without any interference demonstrates the suitability of the sample pretreatment by alkaline hydrolysis. Moreover, it has been no difficulty to determine polysorbate 80 in albumin, a protein which is well-known to bind fatty acids. As polysorbate 80 contains an average of a single fatty acid residue per molecule, a binding of the lipophilic moiety to albumin might occur. Nevertheless, the recoveries in albumin did not give rise to any concerns in this respect.

An interference by low molecular-weight biological compounds as present in plasma (such as e. g. amino acids, sugars, peptides, urea, creatinine) can also be advantageously circumvented by alkaline hydrolysis. Whole plasma for example contains some not further specified components that will not precipitate with ethanol. The suitability of the method of the present invention was demonstrated successfully with plasma approximately half-diluted to a protein content of 30 mg/ml. Thus, the suitability of the alkaline hydrolysis could be proven in very different protein solutions. At the same time, the results of all performed recovery experiments complied with the criteria recommended by the AOAC for peer-verified methods and the found precision enables the introduction of this system as part of quality control programs.

The occurrence of BSE led to a carefully performed check of all auxiliary materials used in the plasma fractionation industry. Plant fats substituted bovine tallow as raw material for the oleic acid in polysorbate 80. Comparing the different source materials used for synthesis with respect to the rather crude fractionation process for the enrichment of oleic acid, it becomes obvious that the fatty acid composition of polysorbates obtained from either bovine or plant fat might differ at least slightly. Most common plant fats are characterized by a higher content of polyunsaturated $C_{18}$ fatty acids in comparison to bovine tallow. It was observed that the polysorbates Tween™ 20 (lauric acid ester), Tween™ 40 (palmitic acid ester), and Tween™ 80 (oleic acid ester) had different complexing properties for thiocyanatocobaltate resulting in a lower extinction of the aqueous complex at 620 nm for Tween™ 80 than for Tween™ 20 and 40. While the fatty acid profile of Tween™ 80 containing ~80% oleic acid is the most homogeneous and significantly different from those of Tween™ 20, 40, and 60 (stearic acid ester), minor differences in the fatty acid composition between plant- and animal-derived polysorbate 80 might most likely explain the measured difference observed as the higher reactivity of the plant-derived material without sample preparation. This explanation is further supported by the fact that such a difference between polysorbates of both sources could be totally eliminated by alkaline hydrolysis (cf. Example 7). This sample treatment will not only result in protein breakdown, but will also cause saponification of the polysorbate resulting in cleavage of the fatty acid moiety from the detergent, which then cannot either bias the colorimetric determination or the extractability of the formed complex. Any variation of the fatty acid moiety of the detergent will no longer influence the determination, and the robustness of the method could be enhanced significantly. Explaining and eliminating this non-expected difference between both polysorbate 80 variants, the basic principle to compare like versus like seems to lose importance in this case and the calibration of the assay can be done using polysorbate 80 irrespective of the source.

With earlier findings of a limit of quantification of 30 ppm polysorbate 80 at 620 nm obtained with a colorimetric method developed for recombinant proteins and not further characterized, the LOQ of 10 ppm polysorbate 80 at 320 nm determined in these experiments agrees well, since the extinction coefficient $\epsilon_{320\,nm}$ is about six-fold higher than $\epsilon 620$ nm. An even more important discovery is the advantageous enhancement of the selectivity by alkaline hydrolysis towards polysorbate. The colorimetric response of the isooctylphenol polyoxyethylene ether Triton™ X-100, as often applied in combination with polysorbate, can be eliminated so far that quantitation of both polyoxyethylated detergents (without hydrolysis for polysorbate and Triton™ X-100 in sum, and for Triton™ X-100 after hydrolysis by subtraction of the residual polysorbate concentration) is made feasible (cf. Example 8). Since the polyoxyethylene phenol ether bridge might most probably be susceptible to alkaline hydrolysis in a similar way as the R-hydroxy alkylphenol ethers in wood lignin, upon ether cleavage a free short polyethylene glycol ($n_{av}$ ~9) chain would be released, of which the thiocyanato-cobaltate complex presumably does not extract quantitatively into the organic phase, but apparently only to at most 1.5%. Thus, even at a concentration of 300 µg/ml triton X-100 shows no measurable interference.

Summarizing all results, with the introduction of the sample pretreatment it is possible to perform a very simple and versatile method for the determination of polysorbate such as polysorbate 80 in the presence of plasma proteins and in addition also in the presence of Triton™ X-100. The method can be performed with appropriate accuracy and precision, thus allowing a determination of the concentration of e.g. polysorbate 80 during the virus inactivation process as well as in the final container. Moreover, the alkaline hydrolysis step primarily designed to enable the performance of the assay in the presence of protein irrespective of the nature of the protein solution turned out to enhance the assay's selectivity in regard to interference by the often applied detergent Triton™ X-100. Finally, the method was also rendered robust against alterations of the fatty acid moiety of polysorbate, of which saponification precluded any contribution to the colorimetric determination.

The invention claimed is:

1. A method for the determination of polysorbate in a protein-containing sample, comprising the steps:
    (a) subjecting the sample to alkaline hydrolysis;
    (b) neutralizing the sample after alkaline hydrolysis;
    (c) optionally removing denatured protein precipitate from the neutralized sample by filtration or centrifation to form a filtered sample;
    (d) adding an aqueous mixture of a thiocyanatometal complex to the optionally filtered sample to form a sorbitan polyoxyethylenethiocyanatometal complex;
    (e) extracting said sorbitan polyoxyethylenethiocyanatometal complex formed in step (d) into a non-water miscible organic solvent;
    (f) measuring the absorbance of the extract obtained in step (e) to quantify the amount of said sorbitan polyoxyethylenethiocyanatometal complex formed in stop (d); and
    (g) calculating the amount of the polysorbate contained in the sample from the amount of said sorbitan polyoxyethylenethiocyanatometal complex determined in step (f).

2. method according to claim 1, wherein the polysorbate is polyoxyethylene sorbitan monooleate (polysorbate 80).

3. The method according to claim 2, wherein the polysorbate 80 originates from animals.

4. The method according to claim 2, wherein the polysorbate 80 originates from plants.

5. The method according to claim 1, wherein the thiocyanatometal complex added in step (d) is an aqueous mixture of $Co(NO_3)_2 \cdot 6\,H_2O$ and $NH_4\,SCN$ and the sorbitan polyoxyethylenethiocyanatometal complex formed is a sorbitan polyoxyethylenethiocyanatocobaltate (II)complex.

6. The method according to claim 5, wherein said aqueous mixture contains about 3% (w/v) $Co(NO_3)_2 \cdot 6\,H_2O$ and about 20% (w/v)$NH_4SCN$.

7. The method according to claim 1, wherein the sample further contains isooctylnhenol polyoxyethylene ether.

8. The method according to claim 1, wherein the sample further contains tri-n-butyl phosphate (TNBP).

9. The method according to claim 1, wherein alkaline hydrolysis in step (a) comprises hydrolysis with an alkaline agent, selected from the group consisting of NaOH, KOH, LiOH, Ba $(OH)_2$, $Sr(OH)_2$, $Ca(OH)_2$, tetrabuthylammonium hydroxide, tetracthylammonimn hydroxide, tetrapropylammonium hydroxide, tetrabutylammonium hydroxide, and homologous or heterologous substituted quaternary alkyl- and cycloalkylammonium hydroxides.

10. The method according to claim 1, wherein alkaline hydrolysis in step (a) is carried out at a temperature in the range of about 80° C. to about 100° C. for at least 15 minutes.

11. The method according to claim 10, further comprising, after step (a) and before step (b) the step:
    (a2) cooling the sample after alkaline hydrolysis.

12. The method according to claim 11, further comprising after step (b) and before step (c) the step:
    (b2) keeping the sample at room temperature for at least 30 minutes to allow the formation denatured protein precipitate.

13. The method according to claim 1, wherein alkaline hydrolysis in step (a) comprises hydrolysis with at least 3 N NaOH at a temperature of about 95° C. to about 100° C. for at least 45 minutes.

14. The method according to claim 1, wherein the filter used in step (c) does not bind polyoxyethylene sorbitan.

15. The method according to claim 1, wherein the non-water miscible organic solvent used in step (e) is selected from the group consisting of methylene chloride, chloroform, o-dichloroberizene, bromoform, and trichloroethylene.

16. The method according to claim 13, wherein the non-water miscible organic solvent is methylene chloride.

17. The method according to claim 1, wherein the absorbance of the extract obtained in step (e) is measured in step (f) at about 324 nm.

\* \* \* \* \*